United States Patent [19]

Oka et al.

[11] Patent Number: 5,886,161
[45] Date of Patent: Mar. 23, 1999

[54] PROCESS FOR PRODUCING AN ALKYLGLYCOSIDE

[75] Inventors: Hiroshi Oka; Kenichi Tachi, both of Wakayama, Japan

[73] Assignee: Kao Corporation, Tokyo, Japan

[21] Appl. No.: 83,110

[22] Filed: May 22, 1998

[30] Foreign Application Priority Data

May 23, 1997 [JP] Japan .................................... 9-133694

[51] Int. Cl.$^6$ .............................. C07G 3/00; C07H 15/04
[52] U.S. Cl. ........................ 536/18.6; 536/18.5; 536/120; 536/124
[58] Field of Search ................................. 536/18.5, 18.6, 536/120, 124

[56] References Cited

U.S. PATENT DOCUMENTS

| 4,950,743 | 8/1990 | McCurry, Jr. et al. . |
| 5,003,057 | 3/1991 | McGurry et al. . |
| 5,717,081 | 2/1998 | Groen . |

FOREIGN PATENT DOCUMENTS

| 90 06933 | 6/1990 | WIPO . |
| 93 24504 | 12/1993 | WIPO . |

*Primary Examiner*—James O. Wilson
*Attorney, Agent, or Firm*—Birch, Stewart, Kolasch & Birch, LLP

[57] ABSTRACT

The process for producing an alkylglycoside, wherein the amount of coarse sugar particles in alkylglycoside can be reduced without reducing reaction yield, is provided.

The process for producing an alkylglycoside comprises,
  a) mixing a hydrated solid sugar with a higher alcohol;
  b) dehydrating the mixture at a reduced pressure at a temperature of lower than a melting point of the hydrated solid sugar until a water content of the solid sugar becomes not more than 0.5% by weight;
  c) heating the mixture to 90°–140° C. so that the proportion of particles having a particle diameter of 0.3 mm or more may be not more than 0.1% by weight of the solid sugar in the mixture at the end of this step;
  d) reacting the mixture with an acid catalyst added thereto at a temperature of 90°–140° C. at a pressure of 5–100 mmHg; and
  e) neutralizing the acid catalyst contained in the product mixture with an alkali after the reaction has been completed.

6 Claims, No Drawings

PROCESS FOR PRODUCING AN ALKYLGLYCOSIDE

TECHNICAL FIELD OF THE INVENTION

The present invention relates to a process for producing an alkylglycoside, more particularly, it relates to a process to efficiently produce alkylglycoside using hydrated solid sugar.

BACKGROUND OF THE INVENTION

Alkylglycosides, which are sugar-derived surfactants, are surfactants less irritant to skin.

One of the conventional processes for producing alkylglycoside is a method wherein sugar and higher alcohol having not less than 8 carbon atoms are directly reacted in the presence of an acid catalyst (hereinafter referred to as "direct method"), and many inventions have been made according to this method. In such direct method, coexistence of sugar and water with an acid catalyst results in a reduced yield and deterioration in color due to by-products such as higher condensate of sugars (hereinafter referred to as "polysaccharides"), which is undesirable. Accordingly, anhydrous sugars free from water such as crystallization water have been generally used as sugar sources.

However, solid sugars containing crystallization water or solid sugars having water absorbed onto their surface (hereinafter referred to as "hydrated solid sugars") are cheaper and economically more advantageous than anhydrous sugars. However, when hydrated solid sugars are used, dehydration should be previously conducted before addition of an acid catalyst because coexistence of water is disadvantageous as mentioned above. As literature describing such dehydration of hydrated solid sugar, for example, U.S. Pat. No. 4,950,743 discloses a method wherein higher alcohol is mixed with hydrated solid sugar, which is kept at high temperature and at low pressure while dehydration is carried out before addition of a catalyst until water content of the mixture falls in the range from 0.1 to 0.25% by weight. WO 90/06933 relates to a process for producing an glycoside with excessive sugars, which discloses that when hydrated solid sugar is used, such sugar is heated at elevated temperature under reduced pressure and dehydrated until water content of the mixture becomes lower than about 0.1% by weight. In addition, WO 93/24504 discloses a method wherein a part of alcohol is previously mixed with hydrated solid sugar, and the mixture is introduced to the rest of alcohol, which had been heated, at a controlled flow rate, then heated at the temperature, at which the sugar becomes syrup, or lower, to dehydrate the mixture until the water content of the mixture becomes 0.5% by weight, after which an acid catalyst is introduced.

PROBLEM TO BE SOLVED BY THE INVENTION

All of the aforementioned conventional techniques employ water content in the mixture as a dehydration set point. However, according to the findings by the present inventors, alkylglycoside cannot be efficiently produced according to direct methods by simply carrying out dehydration until water content of the mixture falls within the desired range. That is, average particle diameter of the generally marketed hydrated solid sugar is about 50 to 150 μm, and by simply conducting dehydration according to the conventional technique, a part of sugar may become coarse particles with diameter up to about 1 to 10 mm (hereinafter referred to as "coarse sugar particles"). Coarse sugar particles have extremely low solubility to higher alcohols. Accordingly, they do not contribute to the reaction with higher alcohol even after addition of an acid catalyst and remain in the reaction mixture, resulting in reduced yield of alkylglycoside. It is very important not to reduce reaction yield for economical production of alkylglycoside.

Further, coarse sugar particles are responsible for troubles such as causing blockage or accumulation in transportation apparatus such as pipeline, pumps or other apparatus constituting process in the alkylglycoside recovering step subsequent to the reaction step (e.g., a step wherein unreacted higher alcohol is distilled off from the reaction mixture). To cope with such troubles, a method may be utilized wherein coarse sugar particles are removed by filtration after the reaction step, but this method is not economical because it requires cost for apparatus and its operation to conduct filtration and is accompanied with reduction in yield due to carry-over loss of alkylglycoside and higher alcohol upon removal of coarse sugar particles. On the other hand, to conveniently remove coarse sugar particles without requiring cost for apparatus and its operation, there is a method wherein a convenient apparatus with wire mesh or perforated panel as filter medium to remove solid impurities, which is called as "strainer, is settled on the transportation pipeline, but many coarse sugar particles may clog filter medium, which requires frequent washing of the filter medium, resulting in extremely reduced labor effectiveness. In addition, alkylglycoside and higher alcohol may also adhere onto the coarse sugar particles, which is inevitably accompanied with reduced yield.

DISCLOSURE OF INVENTION

Accordingly, the object of the present invention is to provide a method which enables efficient production of alkylglycoside at high yield by inhibiting generation of coarse sugar particles to overcome the aforementioned disadvantages.

The present inventors have found that generation of coarse sugar particles can be inhibited by conducting dehydration until water content in the solid sugar in the mixture becomes lower than the defined value and by controlling the proportion of particles with particle diameter larger than the defined value in the solid sugar at the end of the heating step before reaction of the mixture, and have attained the present invention.

That is, the present invention provides a process for producing an alkylglycoside which comprises the steps of;

a) mixing a hydrated solid sugar with a higher alcohol;

b) dehydrating the mixture at a reduced pressure at a temperature of lower than a melting point of the hydrated solid sugar until a water content of the solid sugar becomes not more than 0.5% by weight (hereinafter referred to as 'dehydration step');

c) heating the mixture to 90°–140° C. so that the proportion of particles having a particle diameter of 0.3 mm or more may be not more than 0.1% by weight of the solid sugar in the mixture at the end of this step (hereinafter referred to as 'heating step');

d) reacting the mixture with an acid catalyst added thereto at a temperature of 90°–140° C. at a pressure of 5–100 mmHg (hereinafter referred to as 'reaction step'); and e) neutralizing the acid catalyst contained in the product mixture with an alkali after the reaction has been completed. The conventional techniques have made no suggestion for the aforementioned water content in the solid sugars and proportion of particles with particle diameter of 0.3 mm or more after dehydration. According to the findings by the present inventors, it is extremely important for production of alkylglycoside at high yield to control these values within the aforementioned range. Respective events a) to e) referred to as the term "step" may sequentially occur with time, but the former step should not always be completed before proceeding to the subsequent step.

According to the present invention, dehydration is conducted at the temperature being not higher than the melting point of the hydrated crystalline glucose, while controlling water content retained in the solid sugar to 0.5% by weight or less and the proportion of the particles with particle diameter of 0.3 mm or more in the solid sugar at the beginning of the reaction step to 0.1% by weight or lower, to reduce the amount of particles with particle diameter of 0.3 mm or more to 5% by weight of the solid sugar or less in the reaction mixture at the end of the reaction step, and to reduce the amount of particles with particle diameter of 0.3 mm or more to 0.05% by weight of reaction mixture or less after completion of the reaction step without reducing rate of reaction. Accordingly, troubles during production such as blockage in pipeline can be prevented, thus enabling efficient production of alkylglycoside.

EMBODIMENT OF THE INVENTION

The hydrated solid sugars used in the present invention mean solid sugars containing crystallization water or having water absorbed on their surface as mentioned above, and as sugar sources, any of monosaccharides, oligosaccharides, polysaccharides may be utilized. Monosaccharides include, for example, aldoses such as allose, altrose, glucose, mannose, gulose, idose, galactose, talose, ribose, arabinose, xylose, lyxose; oligosaccharides include, for example, maltose, lactose, sucrose, maltotriose; and polysaccharides include, for example, hemicellulose, inulin, dextrin, dextran, xylan, starch, hydrolyzed starch. Among them, reducing sugars having not more than six carbon atoms are desirable, and glucose is particularly desirable. Particle diameter of hydrated solid sugars used in the present invention may not be particularly limited, but those with average particle diameter of 10 to 250 μm are preferred. "Average particle diameter" herein used means an average value of volume-base distribution of sphere equivalent diameter, which is measured with a particle size measuring device utilizing the principle of light scattering (e.g., LA-500 manufactured by Horiba Seisakusho).

As higher alcohols used in the present invention, straight or branched, saturated or unsaturated alcohols having 8 to 22 carbon atoms or alkylene oxide adducts thereof are preferably used. For example, octyl alcohol, nonyl alcohol, decyl alcohol, lauryl alcohol, tridecyl alcohol, myristyl alcohol, pentadecyl alcohol, cetyl alcohol, heptadecyl alcohol, stearyl alcohol, eicosyl alcohol, oleyl alcohol, or ethylene oxide adducts thereof, propylene oxide adducts thereof.

In the present invention, as for a charging ratio between the starting materials when a hydrated solid sugar and a higher alcohol are mixed, 2 to 10 moles of the higher alcohol per 1 mole of the hydrated solid sugar is preferred. With less than 2 moles of the higher alcohol, a rate of reaction may be reduced. More than 10 moles of higher alcohol may be used, but there is no merit from the technical and economical viewpoints compared with the case using 2 to 10 moles of alcohol.

In the dehydration step, the pressure during dehydration of the mixture of the hydrated solid sugar and higher alcohol under reduced pressure is 10 mmHg to 300 mmHg, preferably 20 mmHg to 200 mmHg. When the pressure is less than 10 mmHg, vaporization rate of the moisture becomes too high, causing loss of the starting material from the system. When the pressure is above 300 mmHg, dehydration becomes insufficient.

The temperature of the mixture during the dehydration step is not lower than 20° C. and lower than melting point of the hydrated solid sugar. At the temperature lower than 20° C., dehydration is insufficient, and when the mixture is exposed to the temperature being higher than melting point of the hydrated solid sugar, the molten sugars may aggregate together in the higher alcohol, and coarse sugar particles may be produced upon dehydration. For example, when the hydrated solid sugar is glucose monohydrate, its melting point is 82° to 85° C. Accordingly, the dehydration step is preferably carried out at 60° to 80° C.

According to the present invention, dehydration is continued at the above temperature and pressure until water content retained in the solid sugar (hereinafter referred to as "water content of solid sugar") becomes 0.5% by weight or lower, preferably 0.3% by weight or lower, more preferably 0.2% by weight or lower. Water content of the solid sugar can be analyzed according to Karl Fischer's titration by sampling the mixture of higher alcohol and hydrated solid sugar, filtering using a glass filter of pore size of 5 to 10 μm, and after washing solid with hexane, removing the adhered hexane at 25° C., 40 mmHg for 10 minutes, and dissolving in an FM solvent (Trade name, "Anhydrated solvent FM" manufactured by Mitsubishi Chemical). During the heating step, coarse sugar particles may be readily formed at the temperature of the mixture higher than the melting point of the hydrated solid sugar when the water content of solid sugar is above 0.5% by weight. The reason is considered that the portion containing water is changed in crystalline structure upon melting and recrystallization, generating coarse sugar particles. Even when the temperature does not exceed the melting point of the hydrated solid sugar during the heating step, water content of the solid sugar above 0.5% by weight may result in production of polysaccharides during the reaction step, also leading to disadvantages such as generation of coarse particles of polysaccharides and reduction in yield.

According to the present invention, the mixture is heated to 90°–140° C. subsequent to the dehydration step. In this step, the mixture is heated to the reaction temperature, and the proportion of particles with particle diameter of 0.3 mm or more should be 0.1% by weight or less of the solid sugar. The proportion of the particles with particle diameter of 0.3 mm or more can be measured by sampling a part of the mixture at the end of the heating step, filtering through a glass filter with pore size of 5 to 10 μm, washing the solid with hexane and drying, then sieving using wire mesh of 0.3 mm sieve opening. According to the findings by the present inventors, when the proportion of the particles with particle diameter of 0.3 mm or more in the solid sugar in the mixture exceeds 0.1% by weight, the aggregation of particles or incorporation of smaller particles into larger particles may be caused, facilitating further enlargement of particles. This may lead to troubles such as reduced reaction yield or blockage in pipeline, as mentioned above.

After completion of the heating step, the reaction is carried out at the temperature of 90° to 140° C., and at the pressure of 5 to 100 mmHg. The temperature is preferably 90° to 120° C. The reaction temperature higher than 140° C. may result in significant deterioration in color as well as significant generation of polysaccharides, resulting in reduced reaction yield. On the other hand, at the temperature below 90° C. reaction rate becomes too low. At the reaction pressure below 5 mmHg, the starting material, higher alcohol, may be readily distilled off, resulting in reduced yield. On the other hand, the pressure above 100 mmHg may result in reduced dehydration efficiency and slow progress of the reaction. The preferred pressure is 20 mmHg to 60 mmHg.

In the present invention, acid catalysts used in the reaction between sugar and higher alcohol include paratoluene sulfonic acid, sulfuric acid, phosphoric acid, strongly acidic ion exchange resin, etc. The amount of the acid catalyst to be used is preferably 0.001 to 0.10 mole per 1 mole of sugar. Below this range, the reaction rate is extremely reduced, and above this range, color of alkylglycoside may become bad.

After completion of the reaction, an acid catalyst in the reaction mixture is neutralized with alkali. Such alkali includes, for example, sodium hydroxide, potassium hydroxide, ammonia, sodium carbonate, etc.

According to the present invention, the proportion of particles with particle diameter of 0.3 mm or more is preferably 5% by weight or less, more preferably 3% by weight or less, particularly preferably 1% by weight or less, of the solid sugar in the reaction mixture at the end of the reaction step. When it exceeds 5% by weight, particles may be readily coarsened due to, for example, aggregation of particles with large particle diameters. In addition, according to the present invention, the proportion of the particles with particle diameter of 0.3 mm or more at the end of the reaction step is preferably 0.05% by weight or less of the reaction mixture. Preferably, the proportion is 0.01% by weight or less, more preferably 0.005% by weight or less. When the proportion exceeds this range, troubles such as blockage or accumulation may be readily occurred in pipeline, apparatus or storage tanks in the subsequent purification step. Even if the coarse particles may be removed using a strainer, operation efficiency may become lower because filter medium is clogged, requiring frequent washing of the filter medium.

Further, according to the present invention, alkylglycoside can be produced at high rate of reaction ("rate of reaction" hereinafter means rate of reaction of sugar (hydrated sugar is calculated in terms of anhydrous sugar) based on the consumed amount), preferably at a rate of reaction of 98.0% or more.

The present invention will be illustrated in detail in the following examples, which is not construed to limit the present invention.

EXAMPLE 1

2000 g of an alcohol mixture of decyl alcohol, lauryl alcohol and myristyl alcohol (weight ratio, 50:35:15) and 471.2 g of hydrated solid glucose having a water content of 9%, determined by dissolving glucose in an FM solvent and analyzing it according to Karl Fischer's titration, having a melting point of 85° C. and an average particle diameter of 112 µm, having trade name: "hydrated crystalline glucose" manufactured by SAN-EI SUCRO CHEMICAL Co., LTD., were charged in a 3 L four-necked glass flask. After initiation of stirring, the pressure in the system was reduced to 35 mmHg, and heating was initiated. To efficiently remove the formed water, nitrogen was blown through the mixture at 20 ml/min. At thirty minutes after beginning of heating, the temperature of the mixture reached 61° C. and water was begun to be distilled off. After that, the temperature reached 78° C. in 45 minutes, and dehydration was conducted maintaining at the temperature for 3 hours. A part of the mixture was sampled, separated into solid and liquid by filtration using a glass filter, and the solid was washed with hexane and dried, and water content of the solid sugar was measured as 0.15% by weight. Water content of the liquid was measured as 0.08% by weight. Subsequently, the mixture was further heated and the temperature reached 105° C. after 25 minutes. The proportion of particles with particle diameter of 0.3 mm or more in the solid sugar was 0% by weight. As an acid catalyst, paratoluene sulfonic acid monohydrate (1.6 g) was added to initiate the reaction. At 9.75 hours after addition of the catalyst, reduced pressure was changed to atmospheric pressure and the acid catalyst was neutralized with NaOH (0.38 g) to terminate the reaction. The rate of reaction reached to 98.5%. No particles with particle diameter of 0.3 mm or more existed in the reaction mixture.

EXAMPLE 2

The procedure of Example 1 was repeated, except that the temperature was maintained for 2.5 hours during the dehydration operation, and the reaction mixture of alkylglycoside was obtained. Water content of the hydrated solid sugar at the end of the dehydration operation was 0.25% by weight, and water content of the liquid phase was 0.07% by weight. After temperature was raised, the proportion of particles with particle diameter of 0.3 mm or more in the solid sugar in the mixture before addition of an acid catalyst was 0.020% by weight. The rate of reaction at the end of the reaction was 98.4%. The amount of particles with particle diameter of 0.3 mm or more in the reaction mixture was 0.0048% by weight, and the proportions of such particles in the solid sugar in the reaction mixture was 1.4% by weight.

EXAMPLE 3

The procedure of Example 1 was repeated, except that the temperature was maintained for 2.0 hours during the dehydration operation, and the reaction mixture of alkylglycoside was obtained. At the end of the dehydration, water content of the solid sugar was 0.34% by weight, and water content of the liquid phase was 0.07% by weight. After temperature was raised, the proportion of particles with particle diameter of 0.3 mm or more in the solid sugar in the mixture before addition of an acid catalyst was 0.021% by weight. The rate of reaction at the end of the reaction was 98.3%. The amount of particles with particle diameter of 0.3 mm or more in the reaction mixture was 0.0056% by weight, and the proportion of such particles in the solid sugar in the reaction mixture was 1.4% by weight.

EXAMPLE 4

The procedure of Example 1 was repeated, except that the temperature was maintained for 1.5 hours during the dehydration operation, and the reaction mixture of alkylglycoside was obtained. At the end of the dehydration, water content of the solid sugar was 0.47% by weight, and water content of the liquid phase was 0.09% by weight. After temperature was raised, the proportion of particles with particle diameter of 0.3 mm or more in the solid sugar in the mixture before addition of an acid catalyst was 0.023% by weight. The rate of reaction at the end of the reaction was 98.3%. The amount of particles with particle diameter of 0.3 mm or more in the reaction mixture was 0.015% by weight, and the proportions of such particles in the solid sugar in the reaction mixture was 1.5% by weight.

Comparative Example 1

The procedure of Example 1 was repeated except that the temperature was maintained for 1.0 hour during the dehydration operation, to obtain the reaction mixture of alkylglycoside. At the end of the dehydration operation, water content of the solid sugar was 0.63% by weight, and water content of the liquid phase was 0.15% by weight. After the temperature was raised, the proportion of particles with particle diameter of 0.3 mm or more in the solid sugar in the mixture before addition of an acid catalyst was 0.68% by weight. The rate of reaction at the end of the reaction was 97.7%. The amount of particles with particle diameter of 0.3 mm or more in the reaction mixture was 0.09% by weight, and the proportions of such particles in the solid sugar in the reaction mixture was 23.1% by weight.

Comparative Example 2

2000 g of an alcohol mixture of decyl alcohol, lauryl alcohol and myristyl alcohol (weight ratio, 50:35:15) and 471.2 g of hydrated crystalline glucose same as that in Example 1 were charged in a 3 L four-necked glass flask. After stirring was initiated, the pressure in the system was reduced to 35 mmHg, and heating was initiated. To efficiently remove the generated water, nitrogen was blown through the mixture at 20 ml/min. At ninety minutes after beginning of heating, the temperature of the mixture reached 105° C. After that, the temperature was retained for an hour. A part of the mixture was sampled, and water content of the solid sugar was measured as 0.31% by weight. Water content of the liquid phase was measured as 0.06% by weight. The proportion of particles with particle diameter of 0.3 mm or more in the solid sugar in the mixture before addition of an acid catalyst was 0.9% by weight. As an acid catalyst, paratoluene sulfonic acid monohydrate (1.6 g) was added to initiate the reaction. At 10 hours after addition of the acid catalyst, reduced pressure was changed to atmospheric pressure and the acid catalyst was neutralized with NaOH (0.33 g) to terminate reaction. The rate of reaction reached to 97.6%. The amount of the particles with particle diameter of 0.3 mm or more in the reaction mixture was 0.12% by weight, and the proportion of such particles in the solid sugars in the reaction mixture was 29.7% by weight.

Comparative Example 3

The procedure of Comparative Example 2 was repeated, except that the temperature was not maintained after the temperature of the mixture reached 105° C. to obtain the reaction mixture of alkylglycoside. When the temperature of the mixture reached 105° C., water content of the solid sugar was 0.61% by weight, and water content of the liquid phase was 0.06% by weight. The proportion of particles with particle diameter of 0.3 mm or more in the solid sugar in the mixture before addition of an acid catalyst was 1.0% by weight. The rate of reaction at the end of the reaction was 97.6%. The amount of particles with particle diameter of 0.3 mm or more in the reaction mixture was 0.13% by weight, and the proportions of such particles in the solid sugar in the reaction mixture was 30.0% by weight. The aforementioned results are summarized in Table 1.

TABLE 1

|  | Ex. 1 | Ex. 2 | Ex. 3 | Ex. 4 | Comparative ex. 1 | Comparative ex. 2 | Comparative ex. 3 |
| --- | --- | --- | --- | --- | --- | --- | --- |
| dehydration temperature (°C.) | 78 | 78 | 78 | 78 | 78 | 105 | 105 |
| dehydration pressure (mmHg) | 35 | 35 | 35 | 35 | 35 | 35 | 35 |
| dehydration temperature pressure-holding time (hr) | 3.0 | 2.5 | 2.0 | 1.5 | 1.0 | 1.0 | 0.0 |
| water content of the solid sugar at the end of the dehydration step (% by weight) | 0.15 | 0.25 | 0.34 | 0.47 | 0.63 | 0.31 | 0.61 |
| water content in the liquid phase at the end of the dehydration step (% by weight) | 0.08 | 0.07 | 0.07 | 0.09 | 0.15 | 0.06 | 0.06 |
| the proportion of particles with particle diameter of 0.3 mm or more in the solid sugar at the beginning of the reaction step (% by weight) | 0.0 | 0.020 | 0.021 | 0.023 | 0.68 | 0.9 | 1.0 |
| rate of reaction (%) | 98.5 | 98.4 | 98.3 | 98.3 | 97.7 | 97.6 | 97.6 |
| the proportion of particles with particle diameter of 0.3 mm or more in the solid sugar at the end of the reaction step (% by weight) | 0.0 | 1.4 | 1.4 | 1.5 | 23.1 | 29.7 | 30.0 |
| the proportion of particles with particle diameter of 0.3 mm or more in the reaction mixture at the end of the reaction step (% by weight) | 0.0 | 0.0048 | 0.0056 | 0.015 | 0.09 | 0.12 | 0.13 |

We claim:

1. A process for producing an alkylglycoside which comprises the steps of:
   a) mixing a hydrated solid sugar with a higher alcohol;
   b) dehydrating the mixture at a reduced pressure at a temperature of lower than a melting point of the hydrated solid sugar until a water content of the solid sugar becomes not more than 0.5% by weight;
   c) heating the mixture to 90°–140° C. so that the proportion of particles having a particle diameter of 0.3 mm or more may be not more than 0.1% by weight of the solid sugar in the mixture at the end of this step;
   d) reacting the mixture with an acid catalyst added thereto at a temperature of 90°–140° C. at a pressure of 5–100 mmHg; and
   e) neutralizing the acid catalyst contained in the product mixture with an alkali after the reaction has been completed.

2. A process as claimed in claim 1, wherein the proportion of the particles having particle diameter of 0.3 mm or more is not more than 5% by weight of the solid sugar in the reaction mixture at the end of the reaction step d).

3. A process as claimed in claim 1, wherein the proportion of the particles having particle diameter of 0.3 mm or more is not more than 0.05% by weight of the reaction mixture at the end of the reaction step d).

4. A process as claimed in claim 1, wherein the hydrated solid sugar is a hydrated glucose.

5. A process as claimed in claim 1, wherein the temperature and the pressure in the dehydration step b) are 60°–80° C. and 10–300 mmHg, respectively.

6. A process as claimed in claim 1, wherein the dehydration is conducted until the water content contained in the solid sugar becomes 0.3% by weight or less in thedehydration step b).

\* \* \* \* \*